United States Patent [19]

Anderson et al.

[11] Patent Number: 5,454,839
[45] Date of Patent: Oct. 3, 1995

[54] LOW PROFILE DEFIBRILLATION CATHETER

[75] Inventors: Kenneth M. Anderson, Bloomington; Mark W. Kroll, Minnetonka, both of Minn.

[73] Assignee: Angeion Corporation, Plymouth, Minn.

[21] Appl. No.: 919,233

[22] Filed: Jul. 27, 1992

[51] Int. Cl.$^6$ .................................................. A61N 1/05
[52] U.S. Cl. ............................................................ 607/123
[58] Field of Search ........................... 128/419 D, 786; 607/122, 123, 119, 5

[56] References Cited

U.S. PATENT DOCUMENTS

| | | | |
|---|---|---|---|
| 3,614,954 | 2/1970 | Mirowski et al. | 128/419 D |
| 3,942,536 | 3/1976 | Mirowski et al. | 128/419 D |
| 4,161,952 | 7/1979 | Kinney et al. | 128/786 |
| 4,355,646 | 10/1982 | Kallok et al. | 128/786 |
| 4,481,953 | 11/1984 | Gold et al. | 607/123 |
| 4,499,907 | 2/1985 | Kallok et al. | 128/786 |
| 4,603,705 | 8/1986 | Speicher et al. | 128/786 |
| 4,640,983 | 2/1987 | Comte . | |
| 4,718,423 | 1/1988 | Willis et al. | 128/634 |
| 4,922,927 | 5/1990 | Fine et al. | 128/786 |
| 4,932,407 | 6/1990 | Williams | 128/419 D |
| 4,974,588 | 12/1990 | Smits | 128/419 D |
| 5,007,436 | 4/1991 | Smits | 607/125 |
| 5,115,818 | 5/1992 | Holleman et al. | 607/122 |
| 5,165,403 | 11/1992 | Mehra | 607/122 |
| 5,265,623 | 11/1993 | Kroll et al. | 607/122 |
| 5,269,319 | 12/1993 | Schulte et al. | 607/123 |

FOREIGN PATENT DOCUMENTS

| | | | |
|---|---|---|---|
| 0491979 | 7/1992 | European Pat. Off. | 607/122 |
| 2009329 | 6/1992 | WIPO | 607/122 |

*Primary Examiner*—Kyle L. Howell
*Assistant Examiner*—Kennedy J. Schaetzle
*Attorney, Agent, or Firm*—Patterson & Keough

[57] ABSTRACT

A low profile defibrillation catheter which is much thinner than existing devices. The thin structure is provided by using the current conductor as the electrode. The thin design is motivated by an electrical field analysis which reveals that the length of the catheter is the important determinant of defibrillation ability, and that the large radius and surface area of prior art devices was not beneficial.

1 Claim, 4 Drawing Sheets

| r (mm) | area cm^2 | Z tot | Z increase |
|---|---|---|---|
| 1 | 5.024 | 57.50 | |
| 1.01 | 5.07424 | 57.38 | 0.21% |
| 1.1 | 5.5264 | 56.36 | |
| 1.99 | 9.99776 | 49.28 | |
| 2 | 10.048 | 49.22 | |
| 2.01 | 10.09824 | 49.16 | |
| 2.02 | 10.14848 | 49.10 | 0.24% |

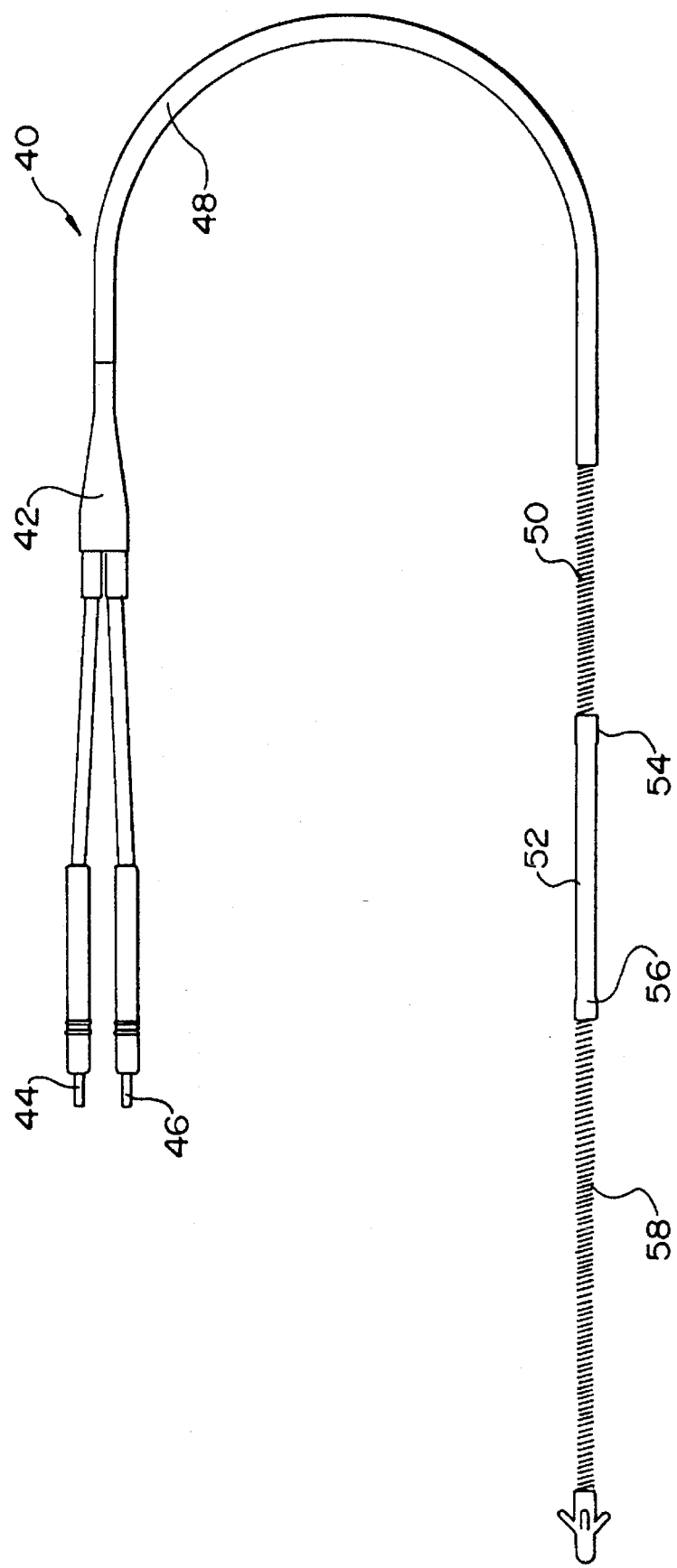

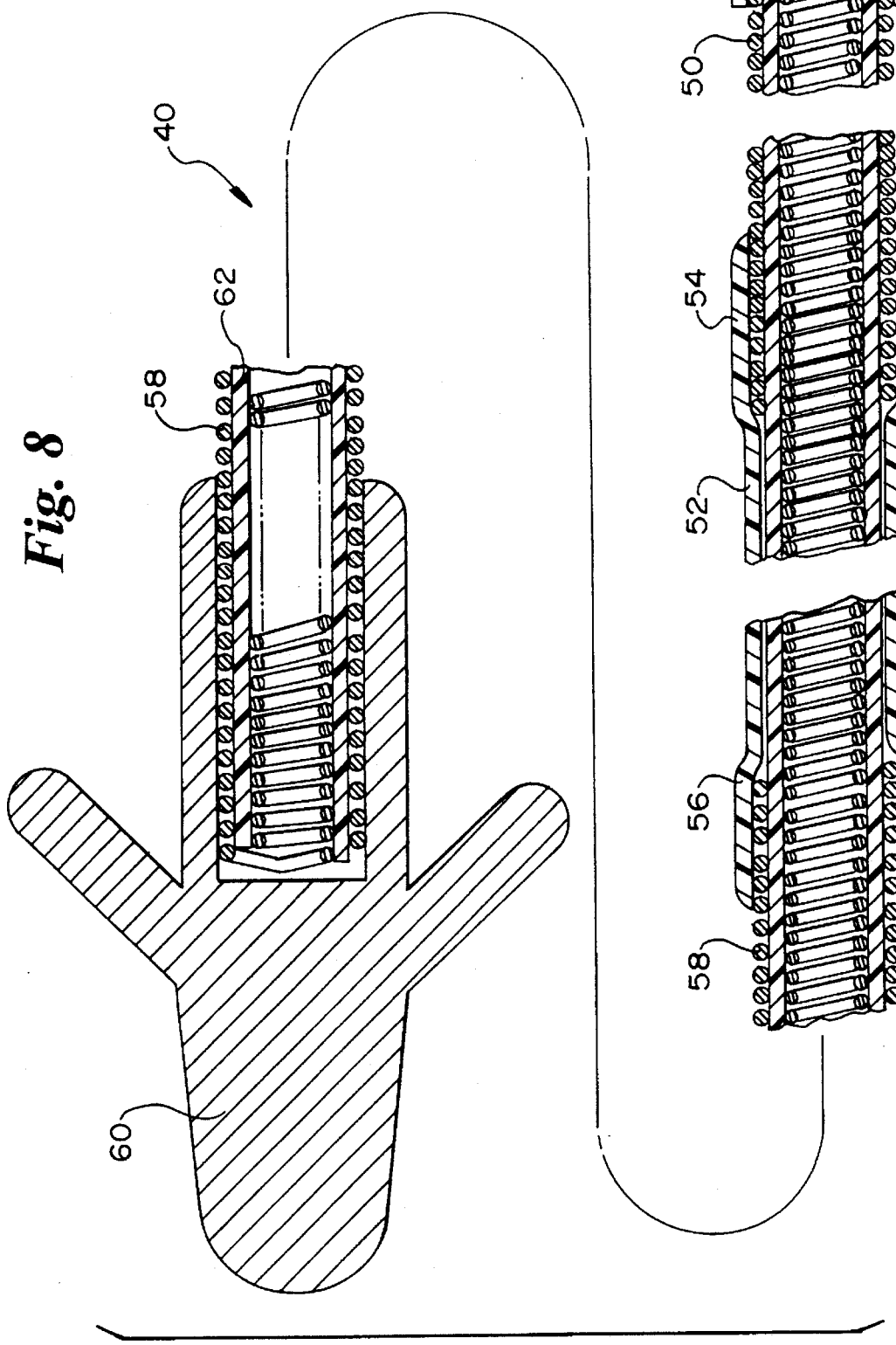

5,454,839

LOW PROFILE DEFIBRILLATION CATHETER

CROSS REFERENCES TO CO-PENDING APPLICATIONS

None.

BACKGROUND OF THE INVENTION

1. Field of the Invention

The present invention pertains to a defibrillation device, and more particularly, refers to a low profile defibrillation catheter where the current conductors are utilized as electrodes.

2. Description of the Prior Art

The implantable defibrillator requires the use of electrodes to conduct large currents through the human heart. These have typically been two or more patches stitched to the heart. These are referred to as epicardial-patch electrodes, and require the surgeon to open the chest cavity for placement.

To avoid the surgery required for the epicardial patches, electrode coils are sometimes passed into the heart chambers. These coils are known as transvenous or catheter electrodes. One coil sits just above the right heart in the right atrium (RA) location, and the other lies in the right ventricular apex (RVA).

Unfortunately, the catheter electrodes are often unable to direct sufficient current through enough of the heart muscle. For this reason, a small patch is often inserted just under the skin, on the patient's lower left side. This requires additional, but minimal, surgery. This "subcutaneous patch" is not in direct contact with the heart, but allows a current vector starting at a transvenous electrode and going through heart muscle. Thus, the subcutaneous patch assists in directing current through the heart muscle, and hence, in defibrillating the heart.

There are two primary electrical requirements for defibrillation electrodes. The first is that the resistance be low enough to allow the passage of the large current through the heart. The second requirement is that the current lines pass through the vast majority of the heart muscle. This requirement is usually met by having sufficient extent to the electrodes and by careful positioning. Thus, the primary opportunity for optimization is in lowering the electrode resistance.

FIG. 1 illustrates a schematic drawing of a patient 10 fitted with a defibrillating system of the prior art consisting of a pulse generator 12 implanted in the abdominal cavity and connected to epicardial-patch electrodes 14 and 16 by electrical-lead harness 18.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 7 illustrates a plan view of the low profile defibrillation catheter; and,

FIG. 8 illustrates a cross-sectional view of the low profile defibrillation catheter.

DESCRIPTION OF THE PREFERRED EMBODIMENTS

Figure 1:
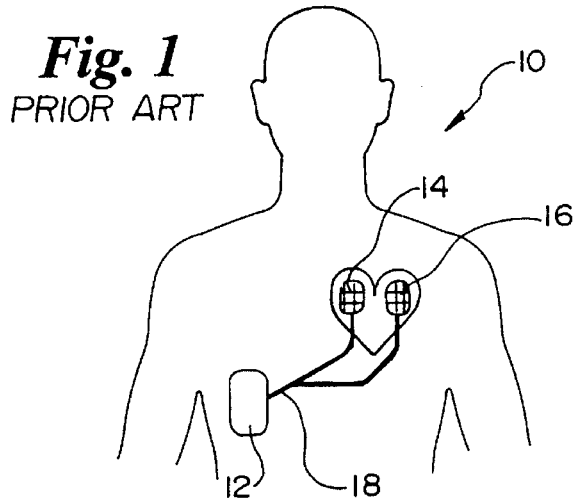
FIG. 1 illustrates a schematic representation of a defibrillating system of the prior art implanted in the abdominal cavity, and having epicardial-patch electrodes attached directly to the heart.
Figure 2:
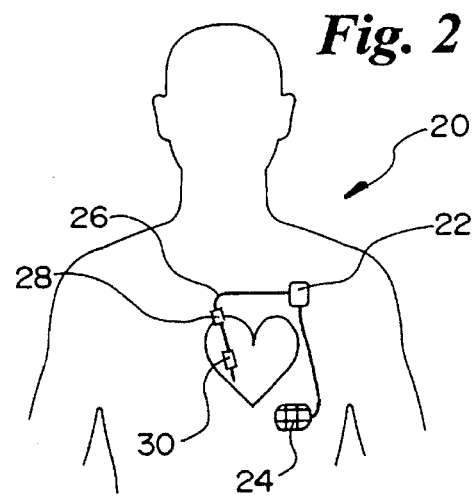
FIG. 2 illustrates a schematic representation of a defibrillating system of the present invention having an SVC electrode, an RVA electrode and one subcutaneous-patch electrode.

FIG. 2 illustrates a schematic drawing of a patient 20 implanted with a defibrillating system including a pectorally implanted pulse generator 22, a subcutaneous-patch electrode 24, and transvenous catheter 26, carrying an SVC electrode 28, and an RVA electrode 30. To avoid the surgery required for the epicardial patches 14 and 16, electrode coils 28 and 30 are passed into the heart chambers. These coils are known as transvenous or catheter electrodes. A coil electrode 28 sits just above the right heart in or at the entrance to the right atrium (RA), and the other coil electrode 30 lies in the right ventricular apex (RVA). Unfortunately, the catheter electrodes are often unable to direct sufficient current through enough of the heart muscle. For this reason, a small subcutaneous-patch electrode 24 is inserted just under the skin, on the patient's lower left side. This requires additional, but minimal, surgery. This "subcutaneous patch" is not in direct contact with the heart, but allows a current vector starting at a transvenous electrode and going through heart muscle. Thus, the subcutaneous patch electrode 24 assists in directing current through the heart muscle, and hence, in defibrillating the heart.

There are two primary electrical requirements for defibrillation electrodes. The first is that the resistance be low enough to allow the passage of the large current through the heart. The second requirement is that the current lines pass through the vast majority of the heart muscle. This requirement is usually met by having electrodes of sufficient extent. Thus, the primary opportunity for optimization is in lowering the electrode resistance.

Figure 3:
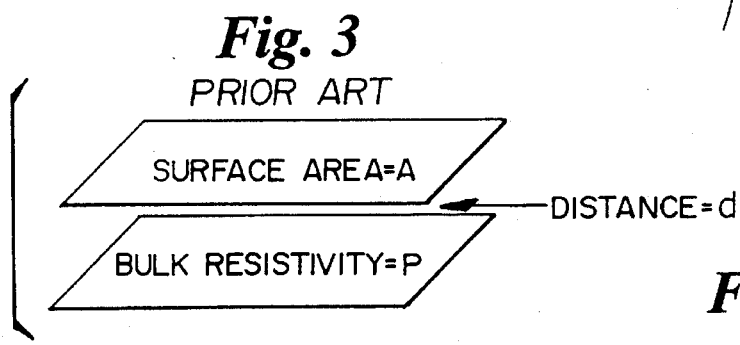
FIG. 3 illustrates a model for estimation of epicardial resistance.

The resistance for epicardial electrodes can be estimated by using standard formulas from physics and the dimensions of the epicardial patches. Consider FIG. 3. The impedance between plates of surface area=A, distance=d, and bulk resistivity=p is given by:

$$Z = \frac{pd}{A} \qquad \text{Eq. 1}$$

and thus, a large surface area is paramount for achieving a low impedance. Typical values are A=30 cm$^2$, d=7 cm and p=150 Ωcm. Thus, a typical impedance for epicardial patches across the heart is:

$$Z = \frac{150 * 7}{30} = 35\Omega \qquad \text{Eq. 2}$$

which is a typical value seen in human implants.

When catheter electrodes were developed it was naturally assumed that a large radius decreased the gap d between it, the internal electrode, and the patch outside the heart. At the same time, a large radius increased the area $2\pi rL$. Thus, designs used diameters that were as large as could be forced into the heart through the often narrow veins. Researchers reported their results with catheter defibrillation using large radius electrodes. Typically where the radius (r)=2 mm and the length (L)=5 cm.

Figure 4:
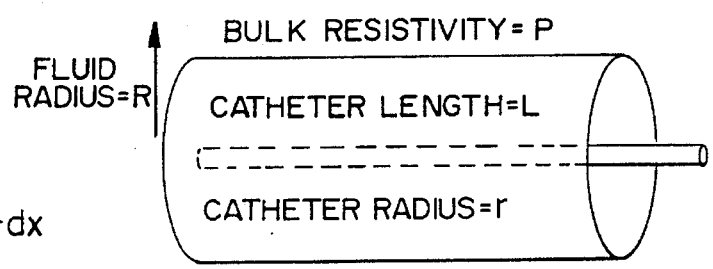
FIG. 4 illustrates a model for estimation of epicardial resistance with respect to a cylindrical shell.
Figure 5:
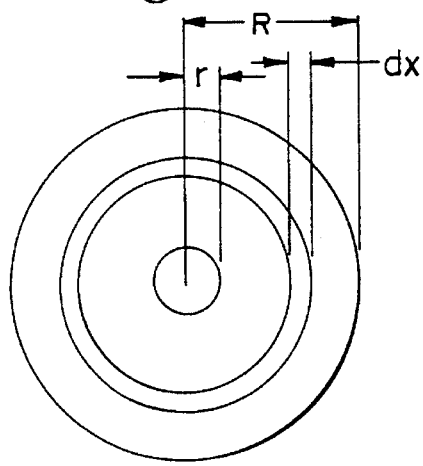
FIG. 5 illustrates the end view of a model for estimation of epicardial resistance with respect to a cylindrical shell.
Figures 6, 9:
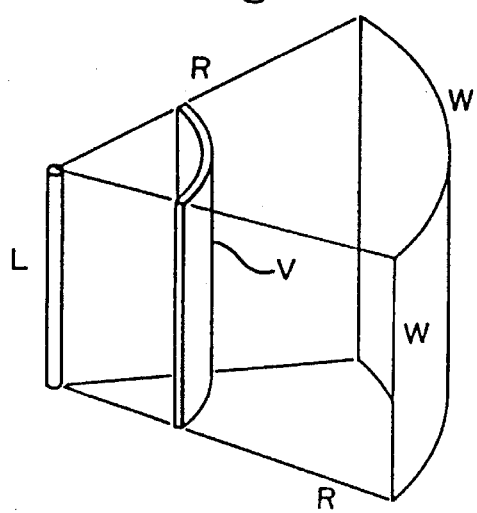
FIG. 6 is a total impedance chart for an electrode system.
FIG. 9 is an impedance model for a defibrillator catheter.

A close inspection of the situation of the defibrillation catheter implanted in the ventricle shows that the impedance model of spaced plates in a fluid is irrelevant. A better model is given in FIG. 4, which shows a catheter of radius=r, length=L, spaced a distance R from a patch W×W. Between L and the patch W×W is an infinitesimal volume (see FIG. 9) with a yet to be determined impedance dZ which can be summed to give an overall impedance Z.

This infinitesimal volume is situated a general, but moveable distance r* from the center of the rod and has an infinitesimal thickness (that is, "gap") dr*. Careful inspection shows that the arc length would be r*W/L and the height L+r*(W–L)/R and multiplied together would be the "area" defined in Eq. 1. So multiplying resistivity p by gap dr*, dividing by "area", and summing (integrating) the infinitesimal volume from r to R, yields:

$$Z = \int_r^R \frac{p\,dr^*}{r^* \frac{W}{R} \left( L + \frac{W-L}{R} r^* \right)} = \frac{Rp}{WL} \ln\left[ \frac{1+Ar}{1+AR} \frac{R}{r} \right] \qquad \text{Eq. 3}$$

Where $A = \frac{W-L}{RL}$

Substituting typical values into the product Ar shows that Ar is small, in the range of –0.01 to +0.01, making the numerator in the log function essentially 1. Using 1 instead of 1–Ar, the above equation simplifies to:

$$Z = \frac{pR}{WL} \ln\left( \frac{R}{r} \frac{L}{W} \right) \qquad \text{Eq. 4}$$

(Substituting typical values into Eq. 4 yields an overall impedance of approximately 100 ohms, which is larger than epicardial patches, but a number very close to that found in clinical tests of transvenous leads.)

This more rigorous inspection, Eq. 4, reveals that impedance is inversely proportional to L and proportional to log of 1/r. The inverse proportionality to L is what conventional thinking suggest, eq. 1, but the log of 1/r entirely changes the situation. Note that the slope of ln(x) is 1/x, meaning that for large x the sensitivity to x (that is, the slope of x) has a weak dependance on x when x is large. And, in our case, x(=RL/rW) is indeed large, approximately 500 (R=10 cm; L=8; r=0.2; W=8).

The sensitivity to r can be shown more vigorously by looking at the percentage change in Z, dZ/Z, as a function of percentage change in r, dr/r. Mathematically, this is done by taking the differential of Eq. 4 and dividing by Z. One finds:

$$\frac{dZ}{Z} = \left( -\ln \frac{RL}{rW} \right)^{-1} \frac{dr}{r} \qquad \text{Eq. 5}$$

Substituting typical values R=10, L=8, r=0.2 and W=8, one gets dZ/Z=–0.16dr/r. The –0.16 factor is very enlightening. It means that a 1% increase in r will decrease impedance only 0.16%, as opposed to L which, because L is inversely proportional to impedance, Eq. 4, a 1% increase in L would cause a full 1% decrease in impedance. Thus, there results a greater impedance benefit, with the same $2\pi rL$ area, for making L as long as possible and r as thin as possible.

In summary, the more careful analysis done here shows that increasing either L or r will decrease impedance, but that L has a much stronger effect on impedance than does r and, therefore, a long, thin electrode is preferable to a short, thick electrode.

In the present invention, the catheter preferably has a maximum diameter of each electrode for a multiple electrode configuration of less than about 10 French (i.e., a maximum diameter <3.3 mm) and preferably less than about 6 French (i.e. a maximum diameter <2 mm) For a single electrode configuration, the maximum diameter of the electrode is less than about 6 French and preferably less than about 4 French. The overall length of the electrode is at least 60 times the radius of the catheter.

FIGS. 7–8 illustrate the details of the construction of the catheter. Note that the conductor is wound continuously to the end of the catheter and is then rewound back over itself to form the actual conductive surface. This is in stark contrast to prior art devices which used different pieces to form the conductor and the electrode. These prior art devices then required crimped or welded connections between the pieces which are a reliability and manufacturability issue, especially if in the areas of highest movement, which are inside the heart itself.

FIG. 7 illustrates a plan view of visible members of the low profile defibrillation catheter 40 including a junction member 42, electrical connectors 44 and 46 extending from the junction member 42, a flexible plastic tubular member 48 extending from the junction member 42, a flexible wound electrode coil member 50 extending from the interior of the flexible plastic tubular member 48, a flexible plastic tubular covering 52 having flared ends 54 and 56 of which flare end 54 accommodates one end of the flexible wound coil electrode member 50, a flexible wound electrode coil member 58 extending from the interior of the flared end 56 and a tined metal catheter tip 60 at the distal end of the flexible wound electrode coil member 58. The connector 44 is electrically connected to the flexible wound electrode coil member 50 and the connector 46 is electrically connected to the flexible wound electrode coil member 58. The flexible wound electrode coil members 50 and 58 align coaxially within the flexible tubular member 48 and the flared end member 54 as described in FIG. 8.

FIG. 8 illustrates a cross-sectional view of the major elements of the low profile defibrillation catheter 40 where all numerals correspond to those elements previously described. The flexible wound electrode coil 50, a flexible plastic tube 62 and an inner minor radius portion of the flexible wound electrode coil member 58 are arranged in a coaxial fashion extending through the flexible tubular member 48 and continuing past the distal end of the flexible tubular member 48 to expose the flexible wound electrode coil member 50 whose distal end secures and terminates suitably within the confines of the flared end 54 of the flexible plastic tubular member 52.

The flexible wound electrode coil member 58 is actually a double layer coil in that it reverses direction at the tined metal catheter tip 60 and is wound back over the flexible plastic tube 62 and ultimately over itself. The flexible wound diameter winding which is aligned within the confines of the flexible plastic tube 62, as just described, and a major diameter winding which is aligned over and about the outer periphery of the flexible plastic tube 62 and subsequently about itself at a finitely spaced distance. After reversal of direction, the major diameter winding of the flexible wound electrode coil member 58 is appropriately terminated between the flexible plastic tube 62 and the flare 56 of the flexible plastic tubular member 52. As illustrated in FIG. 7, it can be seen that the exposure length of the exposed electrode coil wires 50 and 58 is extensive along the length of the low profile defibrillation catheter 40.

Various modifications can be made to the present invention without departing from the apparent scope hereof.

We claim:

1. A multiple electrode cardioversion defibrillation catheter comprising:

a catheter body of dielectric material having two or more electrode coils, each electode coil having a maximum diameter of <10 French (i.e. diameter <3.3 mm); and a first and second electrode conductor longitudinally positioned coaxial with each other in the catheter body, the first electrode conductor surrounding the second electrode conductor for a portion of the catheter body where the first and second electrode conductors are within the dielectric material and terminating at a first electrode coil not having the dielectric material surrounding the first electrode coil, the second electrode conductor extending beyond the first electrode coil where the second electode conductor is within the dielectric material and terminating at a second electrode coil not having the dielectric material surrounding the second electrode coil wherein the second electrode conductor extends to a distal end of the catheter body and continuously extends back toward a proximal end of the catheter body to the second electrode coil such that the second electrode conductor wraps back on top of itself proximal to the distal end of the catheter body.

* * * * *